United States Patent
Deur-Bert et al.

(10) Patent No.: US 10,487,028 B2
(45) Date of Patent: Nov. 26, 2019

(54) METHOD FOR PRODUCING 2-CHLORO-3,3,3-TRIFLUOROPROPENE

(71) Applicant: Arkema France, Colombes (FR)

(72) Inventors: Dominique Deur-Bert, Charly (FR); Dominique Garrait, Charly (FR); Anne Pigamo, Francheville (FR); Laurent Wendlinger, Soucieu en Jarrest (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 16/071,751

(22) PCT Filed: Jan. 13, 2017

(86) PCT No.: PCT/FR2017/050079
§ 371 (c)(1),
(2) Date: Jul. 20, 2018

(87) PCT Pub. No.: WO2017/129878
PCT Pub. Date: Aug. 3, 2017

(65) Prior Publication Data
US 2019/0031584 A1    Jan. 31, 2019

(30) Foreign Application Priority Data
Jan. 28, 2016 (FR) ..................... 16 50673

(51) Int. Cl.
*C07C 17/25* (2006.01)
*C07C 17/20* (2006.01)
*B01J 27/125* (2006.01)

(52) U.S. Cl.
CPC ............. *C07C 17/25* (2013.01); *B01J 27/125* (2013.01); *C07C 17/206* (2013.01)

(58) Field of Classification Search
CPC ....... C07C 17/206; C07C 17/25; C07C 21/18; C07C 17/20; B01J 27/125
See application file for complete search history.

(56) References Cited

U.S. PATENT DOCUMENTS

2015/0203421 A1 * 7/2015 Takahashi ............. C07C 17/206
570/160

FOREIGN PATENT DOCUMENTS

| EP | 2336102 A1 | 6/2011 |
| WO | WO2009015317 A1 | 1/2009 |
| WO | WO2010123154 A2 | 10/2010 |
| WO | WO2012052798 A1 | 4/2012 |

OTHER PUBLICATIONS

ISA/EP, International Search Report and Written Opinion for PCT Patent Application No. PCT/FR2017/050079, dated May 16, 2017.

* cited by examiner

*Primary Examiner* — Jafar F Parsa
(74) *Attorney, Agent, or Firm* — NK Patent Law

(57) ABSTRACT

The invention relates to a method for producing 2-chloro-3,3,3-trifluoropropene (HCFO-1233xf) from at least one compound A selected from the group consisting of halopropane of formulae $CX_3CHClCH_2X$ or $CX_3CFClCH_3$, or halopropenes of formula $CQX_2CCNCH_2$ and $CX_2=CClCH_2X$ where X independently represents a fluorine or chlorine atom, characterised in that it comprises bringing said at least one compound A into contact with HF in a gaseous phase in the presence of a fluorination catalyst $AlF_3$ or fluorine-bearing alumina in order to form a gaseous flow B comprising 2-chloro-3,3,3-trifluoropropene (HCFO-1233xf) et 3,3,3-trifluoropropene (HFO-1243zf).

10 Claims, No Drawings

METHOD FOR PRODUCING 2-CHLORO-3,3,3-TRIFLUOROPROPENE

This application is a U.S. National Stage application of International Application No. PCT/FR2017/050079 filed on Jan. 13, 2017, which claims the benefit of French Patent Application No. 1650673 filed on Jan. 28, 2016, the entire content of all of which is incorporated by reference herein.

The present invention relates to a process for manufacturing 2-chloro-3,3,3-trifluoropropene (HCFO-1233xf) comprising at least one step of gas-phase fluorination in the presence of a catalyst.

On account of its low Global Warming Potential, 2,3,3,3-tetrafluoropropene (HFO-1234yf) is considered as a potential candidate for replacing HFC-134a in motor vehicle air-conditioning.

2,3,3,3-Tetrafluoropropene (HFO-1234yf) may be obtained by reacting 2-chloro-3,3,3-trifluoropropene (HCFO-1233xf) with HF in the presence of a catalyst to give, in a first stage, 1,1,1,2-tetrafluoro-2-chloropropane (HCFC-244bb), and the HCFC-244bb then reacts with HF on a second catalyst (WO 2007/079431).

WO 2010/123154 describes a process for manufacturing HFO-1234yf by reacting HCFO-1233xf with HF in the presence of oxygen using a chromium oxide catalyst of formula $CrO_m$, with $1.5<m<3$, which is optionally fluorinated.

WO 2009/015317 describes a process for manufacturing 2-chloro-3,3,3-trifluoropropene in the presence of a catalyst, $Cr_2O_3$, and of a stabilizer, diisopropylamine. In the absence of stabilizer, the service life of the catalyst is limited.

The Applicant has now developed a process for preparing 2-chloro-3,3,3-trifluoropropene (HCFO-1233xf) which may be used industrially and which does not have the drawbacks of the prior art.

More specifically, the present invention provides a process for manufacturing 2-chloro-3,3,3-trifluoropropene (HCFO-1233xf) starting with at least one compound A chosen from the group consisting of halopropanes of formula $CX_3CHClCH_2X$ or $CX_3CFClCH_3$, or halopropenes of formula $CClX_2CCl=CH_2$ or $CX_2=CClCH_2X$, with X independently representing a fluorine or chlorine atom.

The process according to the present invention comprises placing at least one compound A in contact with HF in the gaseous phase in the presence of a fluorination catalyst to form a gaseous stream B.

According to a preferred embodiment, the fluorination catalyst is $AlF_3$ or a fluorinated alumina; in particular $AlF_3$. The catalyst used may be a bulk or supported catalyst. The support may be active charcoal, magnesium fluoride or zirconium fluoride. According to one embodiment, the fluorination catalyst is $AlF_3$ or fluorinated alumina. Alternatively, the catalyst may also comprise cocatalysts chosen from Ti, V, Mn, Fe, Co, Ni, Cu, Zn, Mg, Ca, Sr, Ba, Zr, Nb, Mo, Pd, Ag, Cd, Sn, Sb, Te, Ta, W, P and Bi, or mixtures thereof. The cocatalyst/catalyst atomic ratio is preferably between 0.01 and 1.

Preferably, the placing in contact is performed in the absence of stabilizer.

According to a preferred embodiment, the stream B comprises 2-chloro-3,3,3-trifluoropropene (HCFO-1233xf) and 3,3,3-trifluoropropene (HFO-1243zf). According to a particular embodiment, the stream B also comprises trichlorofluoropropene (HCFO-1231). The term "trichlorofluoropropene" includes trichlorofluoropropene isomers such as 2,3,3-trichloro-3-fluoropropene (HCFO-1231xf), 1,2,3-trichloro-1-fluoropropene (Z/E-HCFO-1231xb) and 1,1,2-trichloro-3-fluoropropene (HCFO-1231xa). According to a particular embodiment, the stream B also comprises trichlorofluoropropene (HCFO-1232). The term "dichlorofluoropropene" includes dichlorofluoropropene isomers such as 2,3-dichloro-3,3-difluoropropene (HCFO-1232xf), 2,3-dichloro-1,1-difluoropropene (HCFO-1232xc) and 1,2-dichloro-1,3-difluoropropene (HCFO-1232xb). Preferably, the stream B also comprises 2,3-dichloro-2,3-difluoropropene (HCFO-1232xf).

Preferably, the placing in contact is performed at a temperature of between 225° C. and 450° C., in particular between 250° C. and 400° C.

Preferably, the placing in contact is performed with a mole ratio of HF relative to said at least one compound A of between 0.5 and 50 and preferably between 1 and 30.

The placing in contact is generally performed at a pressure of between 0.5 and 20 bar and preferably between 1 and 9 bar.

The placing in contact may be performed for a time of between 1 and 500 hours, preferably between 50 and 400 hours. The contact time may be between 1 and 100 seconds, advantageously between 1 and 75 seconds and preferably between 5 and 50 seconds.

According to one embodiment, said at least one compound A may be at least one halopropane of formula $CX_3CHClCH_2X$ or $CX_3CFClCH_3$ with X independently representing a fluorine or chlorine atom; or a halopropene of formula $CClX_2CCl=CH_2$ or $CX_2=CClCH_2X$ with X representing a chlorine atom.

According to a preferred embodiment, said at least one compound A is chosen from 2,3-dichloro-1,1,1-trifluoropropane (HCFC-243db), 1,1,1,2,3-pentachloropropane (HCC-240db), 2,3,3,3-tetrachloropropene (HCO-1230xf) and/or 1,1,2,3-tetrachloropropene (HCO-1230xa). Preferably, said at least one compound A is chosen from 2,3-dichloro-1,1,1-trifluoropropane (HCFC-243db), 1,1,1,2,3-pentachloropropane (HCC-240db) and/or 1,1,2,3-tetrachloropropene (HCO-1230xa).

Preferably, the present invention provides a process for manufacturing 2-chloro-3,3,3-trifluoropropene (HCFO-1233xf) from 2,3-dichloro-1,1,1-trifluoropropane (HCFC-243db), 1,1,1,2,3-pentachloropropane (HCC-240db), 2,3,3,3-tetrachloropropene (HCFO-1230xf) and/or 1,1,2,3-tetrachloropropene (HCO-1230xa), comprising at least one step of placing in contact as described above.

According to a preferred embodiment, the present invention provides a process for manufacturing 2-chloro-3,3,3-trifluoropropene (HCFO-1233xf) by placing 2,3-dichloro-1,1,1-trifluoropropane (HCFC-243db), 1,1,1,2,3-pentachloropropane (HCC-240db), 2,3,3,3-tetrachloropropene (HCFO-1230xf) and/or 1,1,2,3-tetrachloropropene (HCO-1230xa) in contact with HF in the gaseous phase in the presence of an $AlF_3$ or fluorinated alumina catalyst to form a stream B comprising 2-chloro-3,3,3-trifluoropropene (HCFO-1233xf); advantageously to form a stream B comprising 2-chloro-3,3,3-trifluoropropene (HCFO-1233xf) and 3,3,3-trifluoropropene (HFO-1243zf); preferably to form a stream B comprising 2-chloro-3,3,3-trifluoropropene (HCFO-1233xf), 3,3,3-trifluoropropene (HFO-1243zf) and trichlorofluoropropene (HCFO-1231); in particular to form a stream B comprising 2-chloro-3,3,3-trifluoropropene (HCFO-1233xf), 3,3,3-trifluoropropene (HFO-1243zf), trichlorofluoropropene (HCFO-1231), dichlorodifluoropropene (HCFO-1232) and optionally CO and/or $CO_2$.

According to a particular embodiment, the present invention also provides a process for manufacturing 2-chloro-3, 3,3-trifluoropropene (HCFO-1233xf) by placing 2,3-dichloro-1,1,1-trifluoropropane (HCFC-243db) in contact with HF in the gaseous phase in the presence of an AlF$_3$ or fluorinated alumina catalyst to form a stream B comprising 2-chloro-3,3,3-trifluoropropene (HCFO-1233xf); advantageously to form a stream B comprising 2-chloro-3,3,3-trifluoropropene (HCFO-1233xf) and 3,3,3-trifluoropropene (HFO-1243zf); preferably to form a stream B comprising 2-chloro-3,3,3-trifluoropropene (HCFO-1233xf), 3,3,3-trifluoropropene (HFO-1243zf) and trichlorofluoropropene (HCFO-1231); in particular to form a stream B comprising 2-chloro-3,3,3-trifluoropropene (HCFO-1233xf), 3,3,3-trifluoropropene (HFO-1243zf), trichlorofluoropropene (HCFO-1231), dichlorodifluoropropene (HCFO-1232) and optionally CO and/or CO$_2$.

According to a particular embodiment, the present invention also provides a process for manufacturing 2-chloro-3,3,3-trifluoropropene (HFO-1233xf) by placing 1,1,1,2,3-pentachloropropane (HCC-240db) in contact with HF in the gaseous phase in the presence of an AlF$_3$ or fluorinated alumina catalyst to form a stream B comprising 2-chloro-3,3,3-trifluoropropene (HCFO-1233xf); advantageously to form a stream B comprising 2-chloro-3,3,3-trifluoropropene (HCFO-1233xf) and 3,3,3-trifluoropropene (HFO-1243zf); preferably to form a stream B comprising 2-chloro-3,3,3-trifluoropropene (HCFO-1233xf), 3,3,3-trifluoropropene (HFO-1243zf) and trichlorofluoropropene (HCFO-1231); in particular to form a stream B comprising 2-chloro-3,3,3-trifluoropropene (HCFO-1233xf), 3,3,3-trifluoropropene (HFO-1243zf), trichlorofluoropropene (HCFO-1231), dichlorodifluoropropene (HCFO-1232) and optionally CO and/or CO$_2$.

According to a particular embodiment, the present invention also provides a process for manufacturing 2-chloro-3,3,3-trifluoropropene (HFO-1233xf) by placing 2,3,3,3-tetrachloropropene (HCFO-1230xf) in contact with HF in the gaseous phase in the presence of an AlF$_3$ or fluorinated alumina catalyst to form a stream B comprising 2-chloro-3,3,3-trifluoropropene (HCFO-1233xf); advantageously to form a stream B comprising 2-chloro-3,3,3-trifluoropropene (HCFO-1233xf) and 3,3,3-trifluoropropene (HFO-1243zf); preferably to form a stream B comprising 2-chloro-3,3,3-trifluoropropene (HCFO-1233xf), 3,3,3-trifluoropropene (HFO-1243zf) and trichlorofluoropropene (HCFO-1231); in particular to form a stream B comprising 2-chloro-3,3,3-trifluoropropene (HCFO-1233xf), 3,3,3-trifluoropropene (HFO-1243zf), trichlorofluoropropene (HCFO-1231), dichlorodifluoropropene (HCFO-1232) and optionally CO and/or CO$_2$.

According to a particular embodiment, the present invention also provides a process for manufacturing 2-chloro-3,3,3-trifluoropropene (HFO-1233xf) by placing 1,1,2,3-tetrachloropropene (HCO-1230xa) in contact with HF in the gaseous phase in the presence of an AlF$_3$ or fluorinated alumina catalyst to form a stream B comprising 2-chloro-3,3,3-trifluoropropene (HCFO-1233xf); advantageously to form a stream B comprising 2-chloro-3,3,3-trifluoropropene (HCFO-1233xf) and 3,3,3-trifluoropropene (HFO-1243zf); preferably to form a stream B comprising 2-chloro-3,3,3-trifluoropropene (HCFO-1233xf), 3,3,3-trifluoropropene (HFO-1243zr) and trichlorofluoropropene (HCFO-1231); in particular to form a stream B comprising 2-chloro-3,3,3-trifluoropropene (HCFO-1233xf), 3,3,3-trifluoropropene (HFO-1243zf), trichlorofluoropropene (HCFO-1231), dichlorodifluoropropene (HCFO-1232) and optionally CO and/or CO$_2$.

The stream B may also comprise one or more of the following compounds: 2,3,3,3-tetrachloropropene (HCO-1230xf), 1,1,2,3-tetrachloropropene (HCO-1230xa), 1,1,1,2,3-pentachloropropane (HCC-240db), 1,1,2,3-tetrachloro-1-fluoropropane (HCFC-241db) and/or 1,2,3-trichloro-1,1-difluoropropane (HCFC-242dc).

The stream B obtained may be purified to isolate a stream comprising HCFO-1233xf or may be used in a process for manufacturing 2,3,3,3-tetrafluoropropene (HFO-1234yf). The process according to the present invention may be performed in continuous or batch mode.

According to a particular embodiment, the stream B may be separated to form a gaseous stream D and a liquid phase C. The liquid phase C may comprise 2,3,3,3-tetrachloropropene (HCO-1230xf), 1,1,2,3-tetrachloropropene (HCO-1230xa), 1,1,1,2,3-pentachloropropane (HCC-240db) and/or 1,1,2,3-tetrachloro-1-fluoropropane (HCFC-241db). The liquid phase C may also contain 1,2,3-trichloro-1,1-difluoropropane (HCFC-242dc). The liquid phase C may also comprise 2,3,3-chloro-3-fluoro-propene (HCFO-1231xf), 1,2,3-trichloro-1-fluoropropene (Z/E-HCFO-1231xb) or 2,3-dichloro-3,3-difluoropropene (HCFO-1232xf). The gaseous stream D may comprise 2-chloro-3,3,3-trifluoropropene (HCFO-1233xf), 3,3,3-trifluoropropene (HFO-1243zf), trichlorofluoropropene (HCFO-1231) or dichlorodifluoropropene (HCFO-1232).

EXPERIMENTAL SECTION

The fluorination reactor is charged with a bed of catalyst of AlF$_3$ type. The reaction for the fluorination of HCC-240db is performed at a temperature of between 275 and 375° C. at an absolute pressure of 1 bar. A series of four tests was performed according to the conditions collated in table 1 below.

TABLE 1

| | Experimental conditions | | | |
|---|---|---|---|---|
| Ex. | Temp. (° C.) | HF/240db mole ratio | Contact time (sec) | Contact duration (h) |
| 1 | 275 | 5:1 | 5 | 0-95 |
| 2 | 350 | 5:1 | 5 | 95-170 |
| 3 | 350 | 5:1 | 10 | 170-242 |
| 4 | 375 | 5:1 | 10 | 242-312 |

The stream obtained at the end of the reaction is condensed to form a liquid phase and a gaseous phase. The liquid phase obtained is analysed by $^1$H and $^{19}$F NMR. The results are collated in table 2.

TABLE 2

| NMR data (mol %) based on $^1$H and $^{19}$F NMR. | | | | |
|---|---|---|---|---|
| Products identified | Ex. 1 | Ex. 2 | Ex. 3 | Ex. 4 |
| HFO-1233xf CF$_3$CCl=CH$_2$ | 0.2 | 0.2 | 0.1 | 0.2 |
| HCFO-F1232xf CF$_2$ClCCl=CH$_2$ | 4.3 | 2.4 | 1.6 | 2.3 |
| HCFO-F1231xf CFCl$_2$CCl=CH$_2$ | 6.9 | 6.6 | 7.0 | 8.9 |
| HCFO-F1231xb CH$_2$ClCCl=CFCl | 4.2 | 3.2 | 3.4 | 4.3 |
| HCFO-F1231xa CH$_2$FCCl=CCl$_2$ | 0.4 | 0.5 | 0.3 | 0.2 |
| HCO-F1230xf CCl$_3$CCl=CH$_2$ | 4.3 | 22.3 | 22.9 | 23.0 |

TABLE 2-continued

| NMR data (mol %) based on $^1$H and $^{19}$F NMR. | | | | |
|---|---|---|---|---|
| Products identified | Ex. 1 | Ex. 2 | Ex. 3 | Ex. 4 |
| HCO-F1230xa<br>$CH_2ClCCl=CCl_2$ | 53.3 | 42.7 | 39.2 | 42.2 |
| HCC-F240db<br>$CCl_3CHClCH_2Cl$ | 19.1 | 19.5 | 22.9 | 16.6 |
| HCFC-F241db<br>$CFCl_2CHClCH_2Cl$ | 6.9 | 2.4 | 2.4 | 2.1 |
| HCFC-F242dc<br>$CF_2ClCHClCH_2Cl$ | 0.4 | 0.2 | 0.1 | 0.1 |

The gaseous phase is analysed by GC and GC-MS. The compounds identified in the gaseous phase for Examples 1 to 4 are detailed in table 3 below.

TABLE 3

| Results obtained by on-line GC (mol %) for Examples 1-4 | | | | |
|---|---|---|---|---|
| Products identified[1]<br>(mol %) | Ex. 1 | Ex. 2 | Ex. 3 | Ex. 4 |
| HCFO-F1233xf<br>$CF_3CCl=CH_2$ | 80 | 77 | 86 | 85 |
| HFO-F1243zf<br>$CF_3CH=CH_2$ | 13 | 11 | 9 | 8 |
| HCFO-F1231 and<br>HCFO-F1232 (sum of<br>the isomers) | 7 | 6 | 4 | 3 |
| Other compounds<br>including CO and $CO_2$ | 0 | 6 | 1 | 4 |

[1]mol % of products mentioned is the mean value obtained over the duration of the reaction.

The invention claimed is:

1. A process for manufacturing 2-chloro-3,3,3-trifluoropropene (HCFO-1233xf) starting with at least one compound A comprising a halopropane of formula $CX_3CHClCH_2X$ or $CX_3CFClCH_3$, or halopropenes of formula $CClX_2CCl=CH_2$ or $CX_2=CClCH_2X$ with X independently representing a fluorine or chlorine atom, the process comprising placing said at least one compound A in contact with HF in the gaseous phase at a temperature of between 225° C. and 450° C. in the presence of a fluorination catalyst $AlF_3$ or fluorinated alumina to form a gaseous stream B comprising 2-chloro-3,3,3-trifluoropropene (HCFO-1233xf) and 3,3,3-trifluoropropene (HFO-1243zf).

2. The process as claimed in claim 1, wherein stream B also comprises trichlorofluoropropene (HCFO-1231).

3. The process as claimed in claim 1, wherein stream B also comprises a dichlorodifluoropropene (HCFO-1232).

4. The process as claimed in claim 1, wherein the placing in contact is performed at a temperature of between 250° C. and 400° C.

5. The process as claimed in claim 1, wherein the placing in contact is performed with a mole ratio of HF relative to said at least one compound A of between 0.5 and 50.

6. The process as claimed in claim 1, wherein the placing in contact is performed at a pressure of between 0.5 and 20 bar.

7. The process as claimed in claim 1, wherein the placing in contact is performed in the absence of stabilizer.

8. The process as claimed in claim 1, wherein said at least one compound A is selected from the group consisting of 2,3-dichloro-1,1,1-trifluoropropane (HCFC-243db), 1,1,1,2,3-pentachloropropane (HCC-240db), 2,3,3,3-tetrachloropropene (HCO-1230xf), 1,1,2,3-tetrachloropropene (HCO-1230xa), and mixtures thereof.

9. The process as claimed in claim 1, wherein stream B also comprises 2,3,3,3-tetrachloropropene (HCO-1230xf), 1,1,2,3-tetrachloropropene (HCO-1230xa), 1,1,1,2,3-pentachloropropane (HCC-240db), 1,1,2,3-tetrachloro-1-fluoropropane (HCFC-241db), 1,2,3-trichloro-1,1-difluoropropane (HCFC-242dc) or mixtures thereof.

10. The process as claimed in claim 9, further comprising separating stream B to form a liquid phase C and a gaseous stream D; the liquid phase C comprising 2,3,3,3-tetrachloropropene (HCO-1230xf), 1,1,2,3-tetrachloropropene (HCO-1230xa), 1,1,1,2,3-pentachloropropane (HCC-240db), 1,1,2,3-tetrachloro-1-fluoropropane (HCFC-241db) and 1,2,3-trichloro-1,1-difluoropropane (HCFC-242dc); and the gaseous stream D comprising 2-chloro-3,3,3-trifluoropropene (HCFO-1233xf), 3,3,3-trifluoropropene (HFO-1243zf), trichlorofluoropropene (HCFC-1231) and dichlorodifluoropropene (HCFC-1232).

* * * * *